United States Patent [19]

Brown

[11] 4,254,122
[45] Mar. 3, 1981

[54] TRIAZINE DERIVATIVES

[75] Inventor: Edward D. Brown, Knutsford, England

[73] Assignee: Imperial Chemical Industries Limited, London, England

[21] Appl. No.: 36,508

[22] Filed: May 7, 1979

[30] Foreign Application Priority Data

May 26, 1978 [GB] United Kingdom ............ 22938/78

[51] Int. Cl.³ .................. C07D 251/46; A61K 31/53; C07D 401/04; C07D 401/06
[52] U.S. Cl. .................................. 424/249; 544/211; 544/212
[58] Field of Search .............. 544/194, 211, 212; 424/249

[56] References Cited

U.S. PATENT DOCUMENTS

| | | | |
|---|---|---|---|
| 4,035,365 | 7/1977 | Kay | 544/211 |
| 4,082,536 | 4/1978 | Kay | 544/194 |
| 4,105,433 | 8/1978 | Collins et al. | 544/194 |
| 4,156,002 | 5/1979 | Brown et al. | 544/194 |

FOREIGN PATENT DOCUMENTS 1464248 2/1977 United Kingdom.

Primary Examiner—John M. Ford
Attorney, Agent, or Firm—Cushman, Darby & Cushman

[57] ABSTRACT

The invention concerns new analgesic 6-acylaminotetrahydro-1,3,5-triazine-2,4-dione derivatives of the formula:

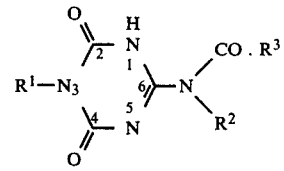

in which $R^1$ is an optionally substituted phenyl, phenyl-(1–4C)alkyl, naphthyl, monocyclic or bicyclic heteroaromatic or (monocyclic or bicyclic heteroaromatic)-(1–4C)alkyl radical, $R^2$ is a (3–8C)cycloalkyl, [(3–8C)cycloalkyl]-(1–4C)alkyl or (3–6C)alkenyl radical, or an optionally substituted phenyl or phenyl-(1–4C)alkyl radical, and $R^3$ is a (1–4C)alkyl radical, preferably a methyl radical; together with pharmaceutically acceptable salts thereof. Also provided are processes for the manufacture of, and pharmaceutical compositions of, derivatives of formula I and salts thereof. Some of the derivatives of formula I possess anti-inflammatory properties and/or are inhibitors of the enzyme prostaglandin synthetase in addition to possessing analgesic properties.

A typical compound of the invention is 3-(thien-2-yl)-6-[(N-acetyl)isobutylamino]tetrahydro-1,3,5-triazine-2,4-dione.

14 Claims, No Drawings

TRIAZINE DERIVATIVES

This invention concerns triazine derivatives and more particularly it concerns 6-acylaminotetrahydro-1,3,5-triazine-2,4-dione derivatives which possess analgesic properties. In addition, certain of the compounds also possess anti-inflammatory properties and/or are inhibitors of the enzyme prostaglandin synthetase.

It is known that certain 3-alkyl-6-acylaminotetrahydro-1,3,5-triazine-2,4-diones posess herbicidal properties (United Kingdom patent specification No. 1,464,248). We have now discovered that certain 6-acylaminotetrahydro-1,3,5-triazine-2,4-dione derivatives which bear an aromatic or heteroaromatic radical at position 3 surprisingly possess useful analgesic properties and in some cases, in addition, possess anti-inflammatory properties and/or are inhibitors of the enzyme prostaglandin synthetase, and herein lies the basis for our invention.

The invention accordingly provides a 6-acylaminotetrahydro-1,3,5-triazine-2,4-dione of the formula:

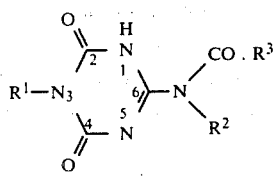

I wherein $R^1$ is a phenyl or phenyl-(1-4C)alkyl radical optionally bearing one or two substituents selected from halogeno, trifluoromethyl, (1-4C)alkyl, (1-4C)-alkoxy, methylenedioxy, (2-5C)alkanoyloxy, nitro, acetyl, cyano, phenyl, halogenophenyl, carboxy, [(1-4C)alkoxy]-carbonyl, (3-6C)alkenyloxy, (2-8C)dialkylamino, and (1-4C)alkylthio substituents, a phenyl radical bearing three, four or five fluoro substituents, or a naphthyl, monocyclic or bicyclic heteroaromatic, or (monocyclic or bicyclic heteroaromatic)-(1-4C)alkyl radical optionally bearing a substituent selected from halogeno, (1-4C)alkyl and (1-4C)alkoxy substituents; and wherein $R^2$ is a (3-8C)alkyl radical, or a (1-4C)alkyl radical bearing one or two (1-4C)alkoxy substituents or bearing a 1,3-dioxalanyl, tetrahydrofuryl or tetrahydropyranyl substituent, or is a (3-8C)cycloalkyl, [(3-8C)cycloalkyl]-(1-4C)alkyl, (3-6C)alkenyl radical, or is a phenyl-(1-4C)alkyl or phenyl radical optionally bearing a substituent selected from halogeno, trifluoromethyl, (1-4C)alkyl and (1-4C)alkoxy substituents; and $R^3$ is a (1-4C)alkyl radical; or a pharmaceutically acceptable base-addition salt thereof; or when $R^1$ is a radical bearing a (2-8C)dialkylamino substituent, a pharmaceutically acceptable acid-addition salt thereof.

It will be appreciated that those compounds of formula I wherein $R^1$ or $R^2$ contain an asymmetric carbon atom, for example those compounds wherein $R^1$ is a 1-(phenyl)ethyl radical, or wherein $R^2$ is 1-(phenyl)ethyl or a sec-butyl radical, and can therefore be isolated in a racemic form or two optically active forms. This specification is addressed to the racemic form of such compounds of formula I or pharmaceutically acceptable salts thereof as defined above, which contain an asymmetrically substituted carbon atom, and to any optical isomer which shows the above mentioned useful properties; it being a matter of general knowledge how to resolve racemic forms or to prepare an optical isomer by direct synthesis from an optically active starting material, and to determine the biological properties of the optical isomers using the standard biological tests mentioned hereinafter.

Certain of the derivatives of formula I may exist in one or more different, discrete crystalline forms, that is they may exhibit the well known phenomenon of polymorphism, for example the derivatives in Examples 79 and 80. As will be appreciated the physical properties of a compound are particularly important when handling material on a large scale, for example during production, purification and formulation of such a compound. It is to be understood that this specification is addressed to compounds of formula I or pharmaceutically acceptable salts thereof as defined above, in any one solid form or a mixture of such forms; it being well known in the art how to determine the physical properties such as melting point and particle size of such forms.

A particular value for $R^1$ when it is a phenyl-(1-4C)alkyl radical is, for example, a benzyl, 1-(phenyl)ethyl or 2-(phenyl)ethyl radical; and when it is a phenyl radical bearing three, four or five fluoro substituents is, for example, a 2,4,6-trifluoro-2,4,5,6-tetrafluoro- or 2,3,4,5,6-pentafluorophenyl radical.

A particular value for $R^1$ when it is a monocyclic heteroaromatic radical is, for example, a fur-2-yl, fur-3-yl, thien-2-yl, thien-3-yl or pyrid-3-yl radical, and when it is a bicyclic heteroaromatic radical is, for example, a quinolin-6-yl, benzthien-2-yl or benzthien-3-yl radical.

A particular value for $R^1$ when it is a (monocyclic or bicyclic heteroaromatic)-(1-4C)alkyl radical is, for example, a (monocyclic or bicyclic heteroaromatic)-methyl, -1-ethyl or -2-ethyl radical in which the monocyclic or bicyclic heteroaromatic moiety is one of the values defined immediately above.

A particular value for $R^2$ when it is a (3-8C)alkyl radical is, for example, an n-propyl, isopropyl, isobutyl, n-butyl, sec-butyl, n-pentyl, pent-2-yl, pent-3-yl or neopentyl radical.

A particular value for $R^2$ when it is a (3-8C)-cycloalkyl radical is, for example, a cyclopropyl or cyclohexyl radical, and when it is a [(3-8C)cycloalkyl]-(1-4C)alkyl radical is, for example, a cyclohexylmethyl radical.

A particular value for $R^2$ when it is a (3-6C)alkenyl radical is, for example, an allyl or 2-methylallyl radical.

A particular value for $R^2$ when it is a phenyl-(1-4C)alkyl radical is, for example, a benzyl, 1-phenylethyl or 2-phenylethyl radical.

Particular values for substituents which may be present on $R^1$ or on $R^2$ as defined above are as follows:
when the substituent is a halogeno, a fluoro, chloro or bromo radical;
when the substituent is a (1-4C)alkyl, a methyl or ethyl radical;
when the substituent is a (1-4C)alkoxy, a methoxy or ethoxy radical;
when the substituent is a (2-5C)alkanoyloxy, an acetoxy, propionyloxy or butyryloxy radical;
when the substituent is a halogenophenyl, a chlorophenyl radical, for example a 4-chlorophenyl radical;
when the substituent is a [(1-4C)alkoxy]carbonyl, a methoxycarbonyl or ethoxycarbonyl radical;
when the substituent is a (3-6C)alkenyloxy, an allyloxy radical;
when the substituent is a (2-8C)dialkylamino, a dimethylamino or diethylamino radical;

when the substituent is a (1–4C)alkylthio, a methylthio radical;
and when the substituent is a 1,3-dioxalanyl, tetrahydrofuryl or tetrahydropyranyl, a 1,3-dioxalan-2-yl, tetrahydrofur-2-yl, tetrahydropyran-2-yl or tetrahydropyran-3-yl radical.

A particular value for $R^3$ is, for example, a methyl, ethyl or propyl radical, of which values a methyl radical is especially preferred.

Specific values for $R^1$ which are special interest are, for example: phenyl, 2-chlorophenyl, 4-chlorophenyl, 4-fluorophenyl, 2,4-difluorophenyl, 2,3,4,5,6-pentafluorophenyl, 3-trifluoromethylphenyl, 2-methylphenyl, 3-methylphenyl, 4-methylphenyl, 4-ethylphenyl, 2,6-dimethylphenyl, 2-methoxyphenyl, 3-methoxyphenyl, 4-methoxyphenyl, 4-ethoxyphenyl, 3,4-methylenedioxyphenyl 4-acetoxyphenyl, 4-nitrophenyl, 4-cyanophenyl, 4-(4-chlorophenyl)phenyl, 4-carboxyphenyl, 4-(ethoxycarbonyl)phenyl, 4-allyloxyphenyl, 4-dimethylaminophenyl, 4-methylthiophenyl, benzyl, 1-(phenyl)ethyl, 4-methoxybenzyl, naphth-2-yl, fur-2-yl, thien-2-yl, thien-3-yl, 2-chloropyrid-3-yl, quinol-6-yl, (thien-2-yl)methyl, (fur-2-yl)methyl and benzthien-2-yl radicals.

A particular value for $R^2$ when it is a substituted (1–4C)alkyl radical is, for example, a substituted methyl, ethyl or propyl radical.

Preferred values for $R^1$ are, for example, when it is a phenyl radical optionally bearing a halogeno, (1–4C)alkyl, (1–4C)alkoxy or trifluoromethyl substituent, and when it is a thien-2-yl radical.

Preferred groups of compounds of formula I comprise those compounds of formula I wherein:
$R^2$ is an isopropyl, isobutyl, sec-butyl or a pent-3-yl radical,
$R^1$ has any of the above defined general or particular values, and $R^3$ is a methyl radical; together with the pharmaceutically acceptable base-addition salts thereof.

A particular pharmaceutically acceptable base-addition salt of a compound of formula I is, for example, an alkali metal or alkaline earth metal salt, for example a sodium, potassium, calcium or magnesium salt, an aluminium salt, for example an aluminium hydroxide disalt, a cooper salt or a complex therewith, or a salt with an organic base affording a pharmaceutically acceptable cation, for example triethanolamine or benzylamine.

A particular pharmaceutically acceptable acid-addition salt of a compound of formula I is, for example, a salt with an inorganic acid, for example, a hydrochloride, hydrobromide or sulphate salt, or a salt with an organic acid affording a pharmaceutically acceptable anion, for example an acetate or citrate salt.

Individual compounds of the invention are described hereinafter in the Examples, and of these the following are of particular interest: 3-(thien-2-yl)-6-[(N-acetyl)-pent-3-ylamino]tetrahydro-1,3,5-triazine-2,4-dione, 3-(thien-2-yl)-6-[(N-acetyl)isobutylamino]tetrahydro-1,3,5-triazine-2,4-dione, 3-(4-methylphenyl)-6-[(N-acetyl)isobutylamino]tetrahydro-1,3,5-triazine-2,4-dione, and 3-(4-methoxyphenyl)-6-[(N-acetyl)isobutylamino]tetrahydro-1,3,5-triazine-2,4-dione, or a pharmaceutically acceptable base addition salt thereof.

The compounds of formula I may be obtained by any process applicable to the manufacture of chemically analogous compounds. Such processes are provided as a further feature of the invention and are illustrated by the following in which $R^1$, $R^2$ and $R^3$ have any of the values defined hereinbefore:

(a) For a compound of the formula I wherein $R^1$ does not bear a carboxy substituent, a compound of the formula:

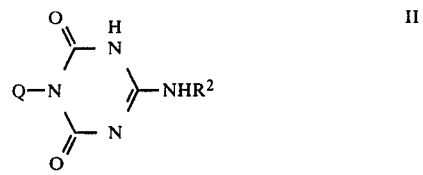

wherein $R^2$ has the meaning defined above and Q has the same value as $R^1$ other than carboxyphenyl and (carboxyphenyl)-(1–4C)alkyl radicals, is reacted with an acylating agent derived from an acid of the formula $R^3CO_2H$.

A suitable acylating agent is, for example, an acid chloride, acid bromide, anhydride or mixed anhydride with formic acid, derived from an acid of the formula $R^3CO_2H$, for example acetyl chloride, acetyl bromide, acetic anhydride, propionic anhydride or butyric anhydride.

The starting materials of formula II may conveniently be obtained as illustrated in the Examples hereinafter by reaction of an amine of the formula $R^2.NH_2$ with a 6-alkylthio-1,3,5-triazine derivative of the formula:

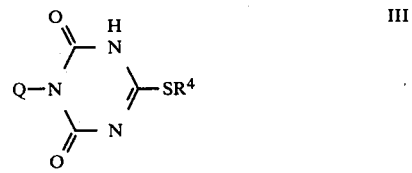

wherein Q has the meaning defined above and $R^4$ is a (1–4C)alkyl radical, for example a methyl radical. The amine of the formula $R^2$-$NH_2$ is conveniently used in the form of its salt with a $C_{1-4}$-alkanoic acid, for example in the form of its acetate salt, and the reaction is preferably carried out at a temperature in the range 100°–250° C.

Those starting materials of formula II wherein Q is a phenyl radical bearing a hydroxy radical may be obtained by dealkylation of the corresponding (1–4C)alkoxy derivative, for example by reaction with hydrobromic acid at a temperature of 50°–150° C.

The 6-alkylthio starting materials of formula III may themselves be obtained by known standard procedures for the synthesis of analogous 1,3,5-triazine-2,4-diones, for example, from the appropriate isocyanates according to the following scheme:

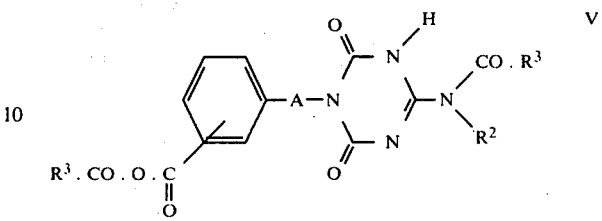

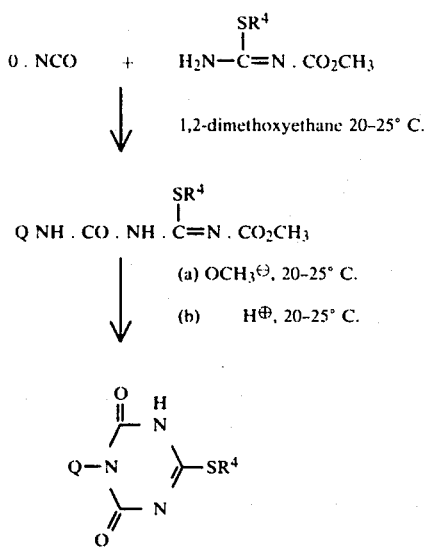

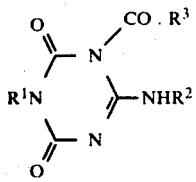

When a compound of formula I wherein $R^1$ is a phenyl radical bearing a (2-5C)alkanoyloxy substituent is required, the starting material may conveniently be a compound of formula II wherein $R^1$ is a phenyl radical bearing a hydroxy substituent, since both O- and N-acetylation of such a compound occurs during the reaction.

(b) A compound of the formula:

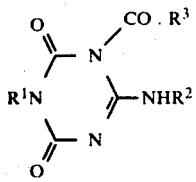

is rearranged.

The rearrangement generally requires elevated temperature, for example 30°-200° C., but in some cases occurs at room temperature, for example at 15°-28° C. The process may optionally be carried out in the presence of a high boiling inert diluent or solvent, for example xylene.

The process may be carried out in the presence of a suitable diluent or solvent, for example a hydrocarbon, for example toluene or xylene, and an excess of acylating agent is preferably used, and may conveniently serve as diluent or solvent. The process may be carried out at a temperature in the range, for example, 60°-200° C., but is preferably carried out in the range 100°-160° C.

The process is particularly suitable for the manufacture of compounds of formula I wherein $R^3$ is a methyl radical, and in which case the required starting materials of formula IV may be obtained by reaction of a compound of formula II with ketene, preferably at, or near, room temperature and in a diluent or solvent, for example methylene chloride. In many cases it is preferable to prepare the compound of formula IV in situ and use it without purification or isolation in process (b). The remaining starting materials of formula IV may be obtained in an analogous manner using the appropriate substituted ketene of the formula $R^5.CH{=}C{=}O$, wherein $R^5$ is a (1-3C)alkyl radical.

(c) For a compound of formula I wherein $R^1$ bears a carboxy substituent, an anhydride of the formula:

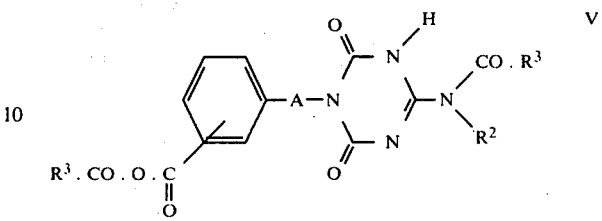

wherein A is a (1-4C)alkylene radical or a direct bond, is hydrolysed.

The hydrolysis is preferably carried out under mild conditions which do not result in hydrolysis of the 6-acylamino radical. The process may therefore conveniently be carried out in a water-miscible solvent, for example ethanol, 2-propanol, tetrahydrofuran or 1,2-dimethoxyethane, in the presence of water at a temperature in the range, for example, 15°-30° C.

The starting materials of formula V may be obtained by acylation of the appropriate compound of formula II but wherein Q is a carboxyphenyl or (carboxyphenyl)-(1-4C)alkyl radical using process (a) hereinabove.

When a pharmaceutically acceptable base-addition salt is required, a compound of formula I is reacted with a suitable base affording a pharmaceutically acceptable cation in a conventional manner. Similarly when a pharmaceutically acceptable acid-addition salt is required, a compound of formula I wherein $R^1$ is a radical bearing a (2-8C)dialkylamino radical is reacted with a suitable acid affording a pharmaceutically acceptable anion in a conventional manner.

The analgesic properties of the compounds of formula I may be demonstrated in a standard test measuring the inhibition of writhing in mice induced by an intraperitoneal injection of acetylcholine, using the procedure of Hacket and Buckett (*European J. Pharmacology*, 1975, 30, 280). In general, compounds of formula I show significant activity in this test at an oral dose of 50 mg./kg., or less, without any overt toxic effects at the active dose, and preferred compounds of formula I show significant activity at an oral dose of 5 mg./kg. or much less.

Alternatively, the analgesic properties of the compounds of formula I may be demonstrated in a standard test involving measurement of inhibition of pain induced by pressure on the foot of a rat into which yeast has previously been injected, based on the procedure of Randall and Selitto (*Arch.int.pharmacodyn.* 1957, 111, 409). In this test compounds of formula I generally show significant activity at an oral dose of 200 mg./kg. or much less without any overt toxic effects at the active dose.

In addition to analgesic properties certain of the compounds of formula I possess anti-inflammatory properties which may be demonstrated using either or both of the following standard tests:

(a) Adjuvant induced arthritis in rats, using a similar procedure to that of B. B. Newbould (*British Journal of Pharmacology*, 1963, 21, 127);

(b) Carrageenin induced oedema in rats using a similar procedure to that of C. A. Winter et alia [*Proceedings*

*of the Society of Experimental Biology* (New York), 1962, 111, 544].

In general compounds of formula I possessing anti-inflammatory properties show activity in either or both of the above tests at an oral dose of 50 mg./kg. or less, given as a daily dose for 14 days in test (a) or as a single dose in test (b), without overt toxic effects at the active dose. An illustrative example of a compound possessing such good additional anti-inflammatory properties is that described in Example 4 hereinafter.

Certain of the compounds of formula I also possess the property of inhibiting the enzyme prostaglandin synthetase. This property may be demonstrated in a standard in vitro test which involves the use of prostaglandin synthetase isolated from the ram seminal vesicle. Those compounds of formula I which inhibit prostaglandin synthetase, in general do so at an in vitro concentration of $10^{-4}$ M or much less, for example, at $10^{-6}$ M. It is known that inhibitors of prostaglandin synthetase, for example indomethacin or flufenamic acid, are clinically effective in the treatment of adverse conditions associated with abnormally high tissue levels of prostaglandins, for example dysmenorrhoea or menorrhagia.

When used to produce the aforementioned pharmacological effects in warm blooded animals the compounds of the invention may be administered as follows:

(a) for analgesic effects, at a daily oral dose of, for example, 0.1–25 mg./kg. of a compound of formula I; (in humans a daily dose of, for example, 5–1500 mg. may be used);

(b) for anti-inflammatory effects, at a daily oral dose of, for example, 1–50 mg./kg. of a compound of formula I possessing anti-inflammatory properties; (in humans a daily dose of, for example, 50–3000 mg. may be used);

(c) to inhibit prostaglandin synthetase in vivo, at a daily dose of, for example, 1–50 mg./kg. of a compound of formula I possessing the property of inhibiting prostaglandin synthetase; (in humans a daily dose of, for example 50–3000 mg. may be used).

The above total daily doses may conveniently be given in divided, but not necessarily equal, doses.

The compounds of the invention are conveniently administered in the form of pharmaceutical compositions, and according to a further feature of the invention there is provided a pharmaceutical composition which comprises a compound of formula I or a pharmaceutically acceptable salt thereof as defined hereinbefore, together with a pharmaceutically acceptable diluent or carrier.

The pharmaceutical composition may be obtained by conventional means using conventional diluents and carriers, and may be in a form suitable for oral administration, for example, in the form of a tablet, capsule, syrup or elixir; or for parenteral administration, for example, in the form of a sterile injectable aqueous suspension or oily solution or suspension; or for rectal administration, for example, in the form of a suppository; or for vaginal administration, for example, in the form of a tampon or pessary.

Convenient dosage unit forms of a composition may contain, for example, 5, 10, 50, 100 or 200 mg. of an active ingredient of formula I or a salt thereof as defined above.

Compositions administered to obtain analgesic or anti-inflammatory effects, for example in the treatment of the painful inflammatory joint diseases, such as rheumatoid arthritis or osteoarthritis, may also contain one or more other agents which can have a beneficial effect on the disease or on associated conditions, for example acetyl salicylic acid, paracetamol, dextropropoxyphene, codeine, chloroquine, phenylbutazone, D-pencillamine, indomethacin, ibuprofen, ketoprofen, naproxen, sulindac, an anti-inflammatory steroid, for example prednisolone, an organogold derivative, or a uricosuric agent, for example probenecid.

The invention is illustrated, but not limited by the following Examples in which:

(i) all evaporations, unless otherwise stated, were carried out by rotary evaporation in vacuo;

(ii) NMR spectral data (where given) was obtained at 60 MHz in $d_6$-DMSO as solvent using tetra-methylsilane as internal standard;

(iii) unless otherwise stated, all procedures were carried out at room temperature i.e. at a temperature in the range 18°–25° C.; and (iv) yields (where given) are purely illustrative and are not to be construed as the maximum attainable for the process illustrated.

EXAMPLE 1

A mixture of 3-(3-trifluoromethylphenyl)-6-n-butylaminotetrahydro-1,3,5-triazine-2,4-dione (4.0 g.) and acetic anhydride (40 ml.) was heated under reflux for 2 hours. The mixture was then distilled at atmospheric pressure over 2 hours, fresh acetic anhydride being added to maintain the original volume. The mixture was then distilled at atmospheric pressure so that the final volume was about 10 ml. Ether (60 ml.) and petroleum ether (b.p. 40°–60° C.) [hereinafter referred to as "40–60 petrol"] (20 ml.) was then added. The white solid which precipitated was washed with ether (2×30 ml.) and air dried to give 3-(3-trifluoromethylphenyl)-6-[(N-acetyl)-n-butylamino]-tetrahydro-1,3,5-triazine-2,4-dione (3.7 g., 66%), m.p. 146°–148° C.

The starting material was obtained as follows:

Methyl N-[1-(amino)-1-(methylthio)methylene]carbamate (14.8 g.) was dissolved in methylene chloride (150 ml.). 3-Trifluoromethylphenyl isocyanate (18.7 g.) was added to the solution during 5 minutes and the mixture was stirred at room temperature for 2.5 hours. A freshly prepared solution of sodium (2.3 g.) in methanol (20 ml.) was then added during 5 minutes and the subsequent mixture was stirred at room temperature for 16 hours. The mixture was then evaporated and the residue was dissolved in water (400 ml.). The aqueous solution obtained, was extracted with ethyl acetate (2×400 ml.) to remove neutral byproducts, and then acidified with concentrated hydrochloric acid to pH1. The solid which precipitated was separated by filtration, washed with water (3×500 ml.), and dried (over phosphorus pentoxide) to give 3-(3-trifluoromethylphenyl)-6-methylthio-tetrahydro-1,3,5-triazine-2,4-dione (25.9 g., 86%) as a white solid, m.p. 225°–228° C.

n-Butylamine (3.92 ml.) was added during 15 minutes to stirred acetic acid (2.4 ml.). After 30 minutes at room temperature, 3-(3-trifluoromethylphenyl)-6-methylthio-tetrahydro-1,3,5-triazine-2,4-dione (6.1 g.) was added to the acetic acid solution. The mixture obtained was then heated at 145° C., for 4 hours. (The liberated methylmercaptan was absorbed into a trap containing an excess of aqueous sodium hydroxide and sodium hypochlorite.) The reaction mixture was cooled to room temperature and then water (75 ml.) was added. The mixture was then stirred for 15 minutes and the white solid which formed was separated by filtration, washed with water (3×150 ml.), and dried (over phosphorus pentoxide) to give 3-(3-trifluoromethylphenyl)-6-n-butylamino-tetrahydro-1,3,5-triazine-2,4-dione (6.0 g., 95%), m.p. 245°-247° C.

EXAMPLES 2-11

Using a similar procedure to that described in Example 1, but starting with the appropriate 4-amino-compound of formula II, the following compounds of formula I ($R^3$ = methyl) were obtained:

| Example | $R^1$ | $R^2$ | m.p.(°C.) | Yield (%) |
|---|---|---|---|---|
| 2 | 3-CF$_3$-phenyl | isobutyl | 119-121 | 66 |
| 3 | 4-MeO-phenyl | isobutyl | 149-151 | 72 |
| 4 | 4-MeO-phenyl | n-butyl | 163-165 | 95 |
| 5 | 4-Me-phenyl | isobutyl | 158-160 | 51 |
| 6 | 4-Me-phenyl | n-butyl | 135-136 | 47 |
| 7 | 2-Cl-phenyl | isobutyl | 135-137 | 69 |
| 8 | 2-Cl-phenyl | n-butyl | 160-161 | 71 |
| 9 | 4-Cl-phenyl | isobutyl | 143-144 | 90 |
| 10 | 4-Cl-phenyl | isopropyl | 115-118 | 70 |
| 11 | 4-Cl-phenyl | benzyl | 220-222 | 42 |

The following starting materials of formula II were obtained in a similar manner to that described in Example I by reacting the appropriate amine of the formula $R^2.NH_2$ with the required compound of formula III wherein $R^4$ is a methyl radical:

| No. | $R^1$ | $R^2$ | m.p.(°C.) | Yield (%) |
|---|---|---|---|---|
| 1 | 3-CF$_3$-phenyl | isobutyl | 272-274 | 95 |
| 2 | 4-Meo-phenyl | isobutyl | 284-285 | 95 |
| 3 | 4-Meo-phenyl | n-butyl | 254-255 | 94 |
| 4 | 4-Me-phenyl | isobutyl | 297-301 | 89 |
| 5 | 4-Me-phenyl | n-butyl | 276-278 | 97 |
| 6 | 2-Cl-phenyl | isobutyl | Note A | 91 |
| 7 | 2-Cl-phenyl | n-butyl | 243-247 | 91 |
| 8 | 4-Cl-phenyl | isobutyl | 297-299 | 94 |
| 9 | 4-Cl-phenyl | isopropyl | 310-312 (decomp.) | 44 |
| 10 | 4-Cl-phenyl | benzyl | Note B | 95 |

Note A:
m.p. >300° C.; NMR (δ): 0.90 (6 protons, d.—CH(CH$_3$)$_2$); 1.85 (1 proton, m.—CH(CH$_3$)$_2$); 3.15 (2 protons, t, N—CH$_2$—CH); 7.3-7.6 (4 aromatic protons, m).Note B:
m.p. >300; NMR (δ): 4.5 (2 protons, d,CH$_2$Ph); 7.28 (s), 7.32 (s), 7.47 (d) [aromatic protons; total 9 protons]; 7.5-7.6 (broad, 1 proton, NH).

The necessary starting materials of formula III ($R^4$ = methyl) were themselves obtained as described in Example 1 by reaction of the appropriate isocyanate with methyl N-[1-(amino)-1-(methylthio)methylene]-carbamate, and had the following properties:

| No. | $R^1$ | m.p.(°C.) | Yield (%) |
|---|---|---|---|
| 1 | 4-MeO-phenyl | 236-237 | 84 |
| 2 | 4-Me-phenyl | 260-265 | 81 |
| 3 | 2-Cl-phenyl | 225-227 | 64 |
| 4 | 4-Cl-phenyl | 286-287 | 74 |

EXAMPLE 12

Using a similar procedure to that described in Example 1, 3-(4-acetoxyphenyl)-6-[N-(acetyl)-n-butylamino]-tetrahydro-1,3,5-triazine-2,4dione was obtained in 51% yield as a solid, m.p. 206°-208° C., but using 3-(4-hydroxyphenyl)-6-n-butylamino-tetrahydro-1,3,5-triazine-2,4-dione as starting material.

The starting material was obtained as follows:
A mixture of 3-(4-methoxyphenyl)-6-n-butylamino-tetrahydro-1,3,5-triazine-2,4-dione (1.0 g.) and hydrobromic acid (48% w/v; 20 ml.) was heated under reflux for 16 hours. The mixture was cooled to room temperature, diluted with water (100 ml.), and the aqueous solution adjusted to pH 6-7 by addition of aqueous sodium hydroxide solution. The white solid produced was separated by filtration, washed with water (3×70 ml.) and dried (over phosphorus pentoxide) to give 3-(4-hydroxyphenyl)-6-n-butylamino-tetrahydro-1,3,5-triazine-2,4-dione (0.5 g., 63%), m.p. 263°-265° C.

EXAMPLE 13

A mixture of 3-(thien-2-yl)-6-isobutylamino-tetrahydro-1,3,5-triazine-2,4-dione (1.4 g.) and acetic anhydride (10 ml.) was heated under reflux for 4 hours. The mixture was then distilled to half volume at atmospheric pressure, cooled to room temperature, and diluted with water (20 ml.). The solid which formed was separated by filtration, washed with water, and then crystallised from ethanol to give 3-(thien-2-yl)-6-[N-(acetyl)isobutylamino]-tetrahydro-1,3,5-triazine-2,4-dione as a white solid (0.6 g., 37%), m.p. 138°-139° C.

The necessary starting materials of formula III and II were obtained in a similar manner to that described in Example 1, but starting with thien-2-yl isocyanate:
(i) 3-(thien-2-yl)-6-methylthio-tetrahydro-1,3,5-triazine-2,4-dione: obtained in 53% yield as a solid, m.p. 220°-222° C.;
(ii) 3-(thien-2-yl)-6-isobutylamino-tetrahydro-1,3,5-triazine-2,4-dione: obtained in 52% yield as a solid, m.p. 265°-268° C.

EXAMPLES 14-16

Using a similar procedure to that described in Example 13, but starting with the appropriate compound of formula II, the following compounds of formula I ($R^3$ = methyl) were obtained:

| Example | $R^1$ | $R^2$ | m.p.(°C.) | Yield (%) |
|---|---|---|---|---|
| 14 | thien-2-yl | n-butyl | 176-178 | 71 |
| 15 | fur-2-yl | isobutyl | 120-122 | 78 |
| 16 | fur-2-yl | n-butyl | 148-150 | 77 |

The necessary starting materials of formula II were obtained from the appropriate amine and compound of formula III, in a similar manner to that described in Example I, and had the following properties:

| No. | $R^1$ | $R^2$ | m.p.(°C.) | Yield (%) |
|---|---|---|---|---|
| 1 | thien-2-yl | n-butyl | 213-215 | 64 |
| 2 | fur-2-yl | isobutyl | 253-255 | 67 |
| 3 | fur-2-yl | n-butyl | 207-210 | 51 |

The remaining starting material of formula III, 3-(fur-2-yl)-6-methylthio-tetrahydro-1,3,5-triazine-2,4-dione, was obtained in 45% yield as a solid, m.p. 188°-190° C., in a similar manner to that described in Example 1, but starting with fur-2-yl isocyanate.

EXAMPLES 17-23

Using a similar procedure to that described in Example 13, the following compounds of formula I ($R^3$ = methyl) were obtained:

| Example | R¹ | R² | m.p.(°C.) | Yield (%) |
|---|---|---|---|---|
| 17 | thien-2-yl | cyclopropyl | 208–210 | 38 |
| 18 | thien-2-yl | pent-3-yl | 152–154 | 23 |
| 19 | thien-3-yl | isobutyl | 180–181 | 44 |
| 20 | thien-3-yl | sec-butyl | 115–117 | 5 |
| 21 | fur-2-yl | cyclopropyl | 211–213 | 87 |
| 22 | fur-2-yl | isopropyl | (a)* | 15 |
| 23 | 2-chloropyrid-3-yl | sec-butyl | (b)* | 39 |

Notes:
*isolated as a glass having satisfactory microanalysis, and NMR spectrum as follows:-

(a): δ, 1.2–1.4 [6 protons, d, —CH(CH₃)₂]; 2.2 (3 protons, S, COCH₃); 4.3–4.67 [1 proton, septuplet, CH(CH₃)₂]; 6.38–6.63 (2 aromatic protons); 7.6–7.7 (1 aromatic proton).

(b): (100MH₂):δ, 0.78–1.0 [3 protons, t, —CH(CH₂CH₃)]; 1.25–1.4 [3 protons, d, CH(CH₃)]; 1.5–2.03 [2 protons, m, CH(CH₂CH₃)]; 2.28 (3 protons, s, COCH₃); 4.17–4.57 [1 proton, m, CH(CH₂CH₃)]; 7.53–7.7 (1 aromatic proton, dd); 8.0–8.16 (1 aromatic proton, dd); 8.43–8.53 (1 aromatic proton, dd).

The necessary starting materials of formula II were obtained in yield of 65–80% in a similar manner to that described in Example 1 by reacting the appropriate amine of the formula R².NH₂ with the required compound of formula III (wherein R³ is a methyl radical):

| No | R¹ | R² | m.p.(°C.) |
|---|---|---|---|
| 1 | thien-2-yl | cyclopropyl | 293–295 |
| 2 | thien-2-yl | pent-3-yl | 240–242 |
| 3 | thien-3-yl | isobutyl | 283–284 |
| 4 | thien-3-yl | sec-butyl | 149–151 |
| 5 | fur-2-yl | cyclopropyl | 265–267 |
| 6 | fur-2-yl | isopropyl | 264–266 |
| 7 | 2-chloropyrid-3-yl | sec-butyl | 282–283 |

The necessary additional starting materials of formula III (R⁴=methyl) wherein R¹ is a thien-3-yl radical and a 2-chloropyrid-3-yl radical were obtained as solids, m.p. 159°–160° C., and 257°–258° C. respectively, in 60–70% yield in a similar manner to that described for the analogous compound in Example 1.

EXAMPLES 24–38

Using a similar procedure to that described in Example 1, the following compounds of formula I (R³=methyl) were obtained:

| Example | R¹ | R² | m.p.(°C.) | Yield(%) |
|---|---|---|---|---|
| 24 | phenyl | isobutyl | 159–161 | 63 |
| 25 | phenyl | n-butyl | 195–197 | 55 |
| 26 | phenyl | pent-3-yl | 116–117 | 50 |
| 27 | 4-Me-phenyl | cyclopropyl | 228–230 | 65 |
| 28 | 4-Me-phenyl | sec-butyl | 120–122 | 6 |
| 29 | 4-Me-phenyl | pent-3-yl | 139–140 | 30 |
| 30 | 4-NO₂-phenyl | isobutyl | 164–166 | 49 |
| 31 | 3-CF₃-phenyl | sec-butyl | (a)* | 59 |
| 32 | 4-MeO-phenyl | sec-butyl | (b)* | 36 |
| 33 | 4-MeO-phenyl | pent-3-yl | (c)* | 41 |
| 34 | 4-MeO-phenyl | phenyl | 234–237 | 88 |
| 35 | 3,4-methylenedioxyphenyl | isobutyl | 174–176 | 70 |
| 36 | 3,4-methylenedioxyphenyl | sec-butyl | 178–180 | 37 |
| 37 | 4-(4-Cl—Ph)-phenyl | isobutyl | 201–203 | 50 |
| 38 | 2,6-dimethylphenyl | isobutyl | 209–211 | 67 |

Notes:
iosolated as a glass having satisfactory microanalysis and NMR spectrum as follows:-

(a) (100MH₂, CDCl₃): δ, 0.82–1.04 [3 protons, t, CH(CH₂CH₃)]; 1.52–1.66 [3 protons, d, CH(CH₃)]; 1.78–2.38 [2 protons, m, CH(CH₂CH₃)] 2.41 (3 protons, s, COCH₃); 4.12–4.52 [1 proton, m, CH(CH₂CH₃)]; 7.4–7.72 (4 aromatic protons).

(b): δ, 0.72–1.03 [3 protons, t, CH(CH₂CH₃)]; 1.2–1.43 [3 protons, d, CH(CH₃)]; 1.5–2.02 [2 protons, m, CH(CH₂CH₃)]; 2.26 (3 protons, s, COCH₃); 3.85 (3 protons, s, CH₃O); 4.07–4.60 [1 proton, m, CH(CH₂CH₃)]; 6.93–7.47 (4 aromatic protons).

(c) (100MH₂): δ, 0.78–1.00 [6 protons, s, CH(CH₂CH₃)]; 1.47–2.04 [4 protons, m, CH(CH₂CH₃)]; 2.30 (3 protons, s, COCH₃); 4.02–4.40 [1 proton, m, CH(CH₂CH₃)]; 3.80 (3 protons, s, CH₃O); 6.92–7.34 (4 aromatic protons).

The starting materials of formula II were obtained in yields of 50–75% in a similar manner to that described in Example 1 and had the following properties:

| No | R¹ | R² | m.p.(°C.) |
|---|---|---|---|
| 1 | phenyl | isobutyl | 273–277 |
| 2 | phenyl | n-butyl | 238–244 |
| 3 | phenyl | pent-3-yl | 269–271 |
| 4 | 4-Me-phenyl | cyclopropyl | 310–312 |
| 5 | 4-Me-phenyl | sec-butyl | 145–147 |
| 6 | 4-Me-phenyl | pent-3-yl | 283–285 |
| 7 | 4-NO₂-phenyl | isobutyl | 272–274 |
| 8 | 3-CF₃-phenyl | sec-butyl | 231–234 |
| 9 | 4-MeO-phenyl | sec-butyl | 272–274 |
| 10 | 4-MeO-phenyl | pent-3-yl | 246–251 |
| 11 | 4-MeO-phenyl | phenyl | 288–291 |
| 12 | 3,4-methylenedioxyphenyl | isobutyl | 282–284 |
| 13 | 3,4-methylenedioxyphenyl | sec-butyl | 259–261 |
| 14 | 4-(4-Cl—Ph)-phenyl | isobutyl | 320–322 |
| 15 | 2,6-dimethylphenyl | isobutyl | 280–290 |

The additional starting materials of formula III (R⁴=methyl) were obtained in 40–45% yields in a similar manner to that described for the analogous compound in Example 1, and had the following characteristic properties:

| No | R¹ | m.p.(°C.) |
|---|---|---|
| 1 | phenyl | 260–265 |
| 2 | 4-NO₂-phenyl | 291–293 |
| 3 | 3,4-methylenedioxyphenyl | 281–283 |
| 4 | 4-(4-Cl—Ph)-phenyl | 301–303 |
| 5 | 2,6-dimethylphenyl | 265–267 |

EXAMPLES 39–40

Using a similar procedure to that described in Example 1, the following compounds of formula I (R³=methyl) were obtained:

| Example | R¹ | R² | Yield (%) | physical properties |
|---|---|---|---|---|
| 39 | 1-phenylethyl, (+)-form | sec-butyl | 57 | gum,[α]$_D^{26}$ + 110° |
| 40 | 1-phenylethyl, (−)-form | sec-butyl | 32 | gum,[α]$_D^{26}$ − 114° |

Both compounds had the following NMR spectrum: (CDCl₃): δ, 0.94 [6 protons, d, CH₂CH(CH₃)₂]; 1.85 (3 protons, d, PhCHCH₃); 2.0–2.3 [1 proton, m, CH₂CH(CH₃)₂]; 2.39 (3 protons, s, COCH₃); 3.83 [2 protons, d, NCH₂CH(CH₃)₂]; 6.07 (1 proton, q, PhCHCH₃); 7.2–7.5 (5 aromatic protons); 12.3 (1 amidic proton).

The necessary starting materials of formula II had the following properties:

| No | R¹ | R² | m.p.(°C.) |
|---|---|---|---|
| 1 | 1-phenylethyl, (+)-form | sec-butyl | 160–162 |
| 2 | 1-phenylethyl, (−)-form | sec-butyl | 161–163 | and were obtained from the corresponding compounds of formula III ($R^3$=methyl) in a similar manner to that described in Example 1 for the analogous intermediates, The intermediates of formula III ($R^4$=methyl) had the following properties:

| No | R¹ | $[\alpha]_D^{26}$ | m.p.(°C.) |
|---|---|---|---|
| 1 | 1-phenylethyl (+)-form | +173 | 176–178 |
| 2 | 1-phenylethyl (−)-form | −174 | 175–179 | and were obtained from (+) and (−)-1-phenylethylisocyanate respectively, and methyl N-[1-amino-1-(methylthio)methylene]carbamate using the procedure described in Example 1.

EXAMPLE 41

A mixture of 3-(4-methylphenyl)-6-isobutylaminotetrahydro-1,3,5-triazine-2,4-dione (20 g.) and acetic anhydride (150 ml.) was heated under reflux with slow distillation for 6 hours, cooled and evaporated. The residual oil solidified in 20 hours and was recrystallised from ethanol (100 ml.) to give 3-(4-methylphenyl)-6-[(N-acetyl) isobutylamino]tetrahydro-1,3,5-triazine-2,4dione (19.4 g., 83%) m.p. 159°–160° C.

The necessary starting materials of formula II and III were obtained as follows:

4-Methylphenylisocyanate (19.0 g.) was added during 10 minutes to a solution of methyl N-[1-amino-1-(methylthio)methylene]carbamate (21.2 g.) in methylene chloride (200 ml.). After 2 hours of stirring, sodium methoxide [obtained by dissolving sodium (3.5 g.) in methanol (30 ml.)] was added at 15°–20° C. The subsequent mixture was stirred at that temperature for 18 hours and the resultant solid collected by filtration and dissolved in water (200 ml.). The solution obtained was acidified with concentrated hydrochloric acid and the solid which formed was collected by filtration, washed well with water and dried to give 3-(4-methylphenyl)-6-methylthiotetrahydro-1,3,5-triazine-2,4-dione (29 g., 81%), m.p. 276°–278° C.

Isobutylamine (1.60 g.) was added to acetic acid (1.20 g.) at 20°–25° C. during 15 minutes. 3-(4-Methylphenyl)-6-methylthiotetrahydro-1,3,5-triazine-2,4-dione (4.98 g.) was then added, and the whole mixture stirred at 120°–125° C. for 5 hours and then cooled. Water (50 ml.) was added and the mixture stirred thoroughly. The solid produced was collected by filtration, washed with water and dried to give 3-(4-methylphenyl)-6-isobutylaminotetrahydro-1,3,5-triazine-2,4-dione (4.90 g., 89%), m.p. 297°–301° C.

EXAMPLES 42–88

Using a similar procedure to that described in Example 13 the following compounds of formula I ($R^3$=methyl) were obtained:

| Example No. | R¹ | R² | m.p.(°C.) | Recrystallization solvent(s) | Yield (%) |
|---|---|---|---|---|---|
| 42 | 4-Et-phenyl | isobutyl | 142–143 | MeOH | 47 |
| 43 | 4-EtO-phenyl | isobutyl | 164–165 | MeOH | 54 |
| 44 | 4-Acetyl-phenyl | isobutyl | 114–115 | MeOH | 16 |
| 45 | 4-Me-phenyl | neopentyl | 175–177 | H₂O/MeOH | 55 |
| 46 | 3-Me-phenyl | isobutyl | 107–109 | EtOH | 72 |
| 47 | 4-allyloxy-phenyl | isobutyl | 112–114 | EtOH | 81 |
| 48 | benzthien-2-yl | isobutyl | 152–153 | EtOH | 83 |
| 49 | 4-MeO-phenyl | cyclohexyl | 155–157 | EtOH | 13 |
| 50 | 4-Me-phenyl | (cyclohexyl)-methyl | 161–162 | EtOH | 79 |
| 51 | 2-Me-phenyl | isobutyl | 150–152 | CH₂Cl₂/40–60 petrol | 52 |
| 52 | 4-cyano-phenyl | isobutyl | 176–178 | CH₂Cl₂/40–60 petrol | 52 |
| 53 | 4-Me-phenyl | 2-methyl-allyl | 180–182 | EtOH | 77 |
| 54 | 4-Me-phenyl | 2-methoxy-ethyl | 162–164 | EtOH | 65 |
| 55 | 4-Me-phenyl | 2-methoxy-propyl | 252–254 | EtOH | 86 |
| 56 | 4-Me-phenyl | 2-phenyl-ethyl | 256–257 (dec.) | MeOH | 26 |
| 57 | 2,4-F₂-phenyl | isobutyl | 137–138 | MeOH | 72 |
| 58 | 4-F-phenyl | isobutyl | 182–184 | MeOH | 62 |
| 59 | 4-F-phenyl | neopentyl | 157–158 | H₂O/MeOH | 64 |
| 60 | 4-F-phenyl | 2,2-dimethoxy-ethyl | 186–187 | EtOH/MeCN | 38 |
| 61 | 4-F-phenyl | cyclohexyl-methyl | 221–223 | MeCN | 62 |
| 62 | pentafluoro- | isobutyl | 122–124 | Et₂O/ | 45 |

-continued

| Example No. | R¹ | R² | m.p.(°C.) | Recrystallization solvent(s) | Yield (%) |
|---|---|---|---|---|---|
| | phenyl | | | 40-60 petrol | |
| 63 | 4-Me-phenyl | 2,2-dimethoxy-ethyl | 176-179 | — | 76 |
| 64 | 4-Me-phenyl | (2-methyl-1,3-dioxolan-2-yl)methyl | 116-118 | H₂O/MeOH | 80 |
| 65 | 4-Me-phenyl | (tetrahydro-furan-2-yl)-methyl | 161-162 | 1,2-di-methoxy-ethane (DME) | 65 |
| 66 | 4-Me-phenyl | (tetrahydro-pyran-2-yl)-methyl | 183-184 | DME | 57 |
| 67 | 4-Me-phenyl | (tetrahydro-pyran-3-yl)-methyl | 165-167 | DME | 63 |
| 68 | 4-MeO-phenyl | neopentyl | 161-162 | H₂O/MeOH | 49 |
| 69 | 4-MeO-phenyl | (2,2-dimethoxy)-ethyl | 172-174 | MeOH | 35 |
| 70 | 4-MeO-phenyl | (cyclohexyl)-methyl | 170-171 | DME | 57 |
| 71 | 4-MeO-phenyl | benzyl | 235-236 | MeOH/MeCN | 36 |
| 72 | 4-MeO-phenyl | 3-CF₃-benzyl | 92-95 | EtOH | 78 |
| 73 | 3-MeO-phenyl | isobutyl | 147-148 | DME | 84 |
| 74 | 3-MeO-phenyl | (cyclohexyl)-methyl | 179-180 | DME | 76 |
| 75 | 2-MeO-phenyl | isobutyl | 192-194 | DME | 63 |
| 76 | 2-MeO-phenyl | neopentyl | 139-141 | H₂O/MeOH | 13 |
| 77 | 4-MeO-phenyl | isobutyl | 152-154 | DME | 71 |
| 78 | naphth-1-yl | isobutyl | 171-172 | MeOH | 74 |
| 79 | naphth-1-yl | neopentyl | 108-122 [Note (A)] | i-PrOH | 44 |
| 80 | quinol-6-yl | isobutyl | 135-150 [Note (B)] | MeOH | 30 |
| 81 | quinol-6-yl | n-butyl | 180-181 | MeOH | 54 |
| 82 | benzyl | isobutyl | 93-94 | Et₂O/MeOH | 51 |
| 83 | benzyl | (cyclohexyl)-methyl | 125-126 | MeOH | 67 |
| 84 | 4-MeO-benzyl | isobutyl | 63-66 (hemi-hydrate) | Et₂O/40-60 petrol | 66 |
| 85 | (thien-2-yl)-methyl | isobutyl | 100-102 | Et₂O | 34 |
| 86 | (fur-2-yl)-methyl | isobutyl | 103-104 | Et₂O/MeOH | 56 |
| 87 | (fur-2-yl)-methyl | (cyclohexyl)-methyl | 161-162 | MeCN | 64 |
| 88 | 4-(ethoxy-carbonyl)-phenyl | isobutyl | 191-193 | CH₂Cl₂/40-60 petrol | 63 |

Note (a):
mixture of polymorphs; microanalysis, found: C, 65.4, H, 6.1; N, 15.1, required: C, 65.6, H, 6.0, N, 15.3%

Note (b):
mixture of polymorphs; microanalysis, found: C, 61.1; H, 5.3, N, 19.8; required: C, 61.2, H, 5.4; N, 19.8%.

The necessary starting materials of formula II were obtained in yields in the range 50-95% using a similar procedure to that described for the analogous starting materials in Examples 1 and 41, and had the following characteristics:

| No. | R¹ | R² | m.p.(°C.) |
|---|---|---|---|
| 1 | 4-Et-phenyl | isobutyl | 274-275 |
| 2 | 4-EtO-phenyl | isobutyl | 284-286 |
| 3 | 4-Acetylphenyl | isobutyl | 256-258 |
| 4 | 4-Me-phenyl | neopentyl | 296-298 |
| 5 | 3-Me-phenyl | isobutyl | 277-280 |
| 6 | 4-allyloxy-phenyl | isobutyl | 261-264 |
| 7 | benzthien-2-yl | isobutyl | 272-274 |
| 8 | 4-MeO-phenyl | cyclohexyl | 302-304 |
| 9 | 4-Me-phenyl | (cyclohexyl)-methyl | 297-299 |
| 10 | 2-Me-phenyl | isobutyl | 266-267 |
| 11 | 4-cyanophenyl | isobutyl | 277-279 |
| 12 | 4-Me-phenyl | 2-methylallyl | 267-269 |
| 13 | 4-Me-phenyl | 2-methoxyethyl | 242-244 |
| 14 | 4-Me-phenyl | 2-methoxypropyl | 252-254 |
| 15 | 4-Me-phenyl | 2-phenylethyl | 290-291 (dec.) |
| 16 | 2,4-F₂-phenyl | isobutyl | 285-287 |

-continued

| No. | R¹ | R² | m.p.(°C.) |
|---|---|---|---|
| 17 | 4-F-phenyl | isobutyl | 293–294 |
| 18 | 4-F-phenyl | neopentyl | 308–310 |
| 19 | 4-F-phenyl | 2,2-dimethoxy-ethyl | 280–281 |
| 20 | 4-F-phenyl | cyclohexyl-methyl | 302–303 |
| 21 | pentafluoro-phenyl | isobutyl | 254–257 |
| 22 | 4-Me-phenyl | 2,2-dimethoxy-ethyl | 188–189 |
| 23 | 4-Me-phenyl | (2-methyl-1,3-dioxolan-2-yl)-methyl | 236–238 |
| 24 | 4-Me-phenyl | (tetrahydrofuran-2-yl)methyl | 268–269 |
| 25 | 4-Me-phenyl | (tetrahydropyran-2-yl)methyl | 283–284 |
| 26 | 4-Me-phenyl | (tetrahydropyran-3-yl)methyl | 243–246 |
| 27 | 4-MeO-phenyl | neopentyl | 299–300 |
| 28 | 4-MeO-phenyl | (2,2-dimethoxy)-ethyl | 183–184 |
| 29 | 4-MeO-phenyl | (cyclohexyl)-methyl | 280–281 |
| 30 | 4-MeO-phenyl | benzyl | 258–259 |
| 31 | 4-MeO-phenyl | 3-CF₃-benzyl | 257–258 |
| 32 | 3-MeO-phenyl | isobutyl | 216–219 |
| 33 | 3-MeO-phenyl | (cyclohexyl)-methyl | 263–265 |
| 34 | 2-MeO-phenyl | isobutyl | 241–243 |
| 35 | 2-MeO-phenyl | neopentyl | 273–275 |
| 36 | 4-MeO-phenyl | isobutyl | 273–274 |
| 37 | naphth-1-yl | isobutyl | 277–279 |
| 38 | naphth-1-yl | neopentyl | 309–312 |
| 39 | quinol-6-yl | isobutyl | 278–279 |
| 40 | quinol-6-yl | n-butyl | 266–269 |
| 41 | benzyl | isobutyl | 265–266 |
| 42 | benzyl | (cyclohexyl)-methyl | 300–302 |
| 43 | 4-MeO-benzyl | isobutyl | 265–266 |
| 44 | (thien-2-yl)-methyl | isobutyl | 274–276 |
| 45 | (fur-2-yl)-methyl | isobutyl | 264–266 |
| 46 | (fur-2-yl)-methyl | (cyclohexyl)-methyl | 283–286 |

The necessary starting materials of formula III ($R^4$=methyl) were obtained by reacting the appropriate isocyanate of the formula $R^1$.NCO with methyl [1-amino-1-(methylthio)methylene]carbamate as described in Example 1. Where the necessary isocyanates were not commercially available they were either prepared by reaction of the corresponding amino of the formula $R^1NH_2$ with phosgene (Route A) or by thermal decomposition of the corresponding acid azide of the formula $R^1.CO.N_3$ (Route B). In either case the subsequently formed isocyanates were used in situ without isolation.

Route A is illustrated by the following preparation:

A solution of furfurylamine (22.0 g.) in dry toluene (40 ml.) was added at room temperature during 45 minutes to a stirred solution of phosgene (12.5 % w/w) in toluene (230 ml.). The mixture was gradually warmed to reflux temperature during 90 minutes and then heated under reflux for the same period. The mixture was cooled and separated by filtration. The black residue was discarded and the filtrate which contained furfuryl isocyanate was added to a stirred solution of methyl N-[1-amino-1-(methylthio)methylene]carbamate (33.6 g.) in dry methylene chloride (750 ml.) during 45 minutes. The subsequent mixture was stirred at room temperature for 1.75 hours and then a fresh solution of sodium (6.0 g.) in methanol (60 ml.) was added, and the basic mixture stirred for 60 hours. The white solid which deposited was collected and dissolved in water (700 ml.). The solution was extracted with ethyl acetate (2×300 ml.) and the extracts discarded. The aqueous phase was acidified to pH 1 with concentrated hydrochloric acid to give 3-furfuryl-6-methylthiotetrahydro-1,3,5-triazine-2,4-dione as a white solid (20.8 g.), m.p. 209°–211° C.

Route B is illustrated by the following preparation:

Sodium azide (9.0 g.) was added to a stirred solution of 4-methylthiobenzoyl chloride (23.3 g.) [obtained as a solid, m.p. 48°–50° C., by reaction of 4-methylthiobenzoic acid with excess thionyl chloride catalysed by dimethylformamide, followed by evaporation of the residual thionyl chloride] in dry 1,2-dimethoxyethane (DME) (100 ml.), and the mixture stirred at room temperature for 18 hours. The solid (sodium chloride) which formed was separated by filtration and washed with DME (15 ml.). The combined washings and filtrate (which contained 4-methylthiobenzoylazide) were warmed to 80° C. with stirring for 4 hours after which time gas evolution had stopped, and conversion to 4-methylthiophenyl isocyanate was complete. The solution was then treated with methyl N-[1-amino-1-(methylthio)methylene]carbamate (16.3 g.) and the mixture stirred for 18 hours at room temperature. A fresh solution of sodium (2.9 g.) in methanol (45 ml.) was then added and the mixture stirred for a further 18 hours. The resultant mixture was evaported and the residue treated with water (250 ml.) and ethyl acetate (100 ml.). The mixture was separated and the aqueous phase extracted with ethyl acetate (100 ml.). The aqueous phase was then separated and acidified to pH 1–2 with concentrated hydrochloric acid to give 3-(4-methylthio-phenyl)-6-methylthiotetrahydro-1,3,5-triazine-2,4-dione as a white solid (26.7 g.), m.p. 243°–246° C.

The following starting materials of formula III ($R^4$=methyl) were obtained by generally similar procedures except that in some cases commercial samples of isocyanates were used as described in Example 1 and 13 (indicated as Route C in the Table below):

| No. | R¹ | m.p.(°C.) | Route |
|---|---|---|---|
| 1 | 4-Et-phenyl | 254–256 | B |
| 2 | 4-EtO-phenyl | 278–279 (dec.) | B |
| 3 | 3-Acetyl-phenyl | 296–298 (dec.) | A |
| 4 | 3-Me-phenyl | 209–214 | C |
| 5 | 4-allyloxyphenyl | 238–240 | A |
| 6 | benzthien-2-yl | 222–226 | B |
| 7 | 2-Me-phenyl | 199–201 | C |
| 8 | 4-cyanophenyl | 214–216 | B |
| 9 | 2,4-F₂-phenyl | 221–222 | A |
| 10 | 4-F-phenyl | 275–276 | C |
| 11 | pentafluoro-phenyl | 268–270 | C |
| 12 | 3-MeO-phenyl | 237–239 | C |
| 13 | 2-MeO-phenyl | 127–130 | C |
| 14 | naphth-1-yl | 195–197 | C |
| 15 | quinol-6-yl | 270–273 | A* |
| 16 | benzyl | 220–222 | A |
| 17 | 4-MeO-benzyl | 221–224 | A |
| 18 | (thien-2-yl)-methyl | 226–227 | A |

*Tetrahydrofuran rather than methylene chloride used as solvent.

The starting material of formula II for Example 88 was obtained as follows:

A mixture of 3-(4-cyanophenyl)-6-isobutylaminotetrahydro-1,3,5-triazine-2,4-dione (15.0 g.) and ethanol (800 ml.) saturated with hydrogen chloride was heated under reflux for 24 hours. The mixture was evaporated and water (200 ml.) added to the residue followed by saturated aqueous sodium acetate solution until pH 4 was attained. The solid which formed was collected by filtration, washed with water and dried to give 3-[(4-ethoxycarbonyl)phenyl]-6-isobutylaminotetrahydro-1,3,5-triazine-2,4-dione (14.2 g.), m.p. 260°–262° C.

EXAMPLE 89

A solution of 3-[4-(acetoxycarbonyl)phenyl]-6-[(N-acetyl)isobutylamino]tetrahydro-1,3,5-triazine-2,4-dione (2.6 g.) in 1,2-dimethoxyethane (20 ml.) containing water (2 ml.) was left for 20 hours and then evaporated. The residue was pressure-chromatographed on silica using a mixture of 44 parts by volume of ethyl acetate and 1 part by volume of acetic acid to yield 3-(4-carboxyphenyl)-6-[(N-acetyl)isobutylamino]tetrahydro-1,3,5-triazine-2,4-dione (0.9 g., 39%), m.p. 191°–193° C.

The starting material was obtained as follows:

A mixture of 3-(4-cyanophenyl)-6-isobutylaminotetrahydro-1,3,5-triazine-2,4-dione (2.5 g.) and concentrated hydrochloric acid (100 ml.) was heated at 100° C. for 16 hours and was then evaporated. Water was added to the residue and the resultant colourless solid was collected by filtration, washed with water and dried to give 3-(carboxyphenyl)-6-isobutylaminotetrahydro-1,3,5-triazine-2,4-dione (2.0 g., 75%), m.p. >300° C. This solid was heated under reflux with excess acetic anhydride for 8 hours and then the mixture evaporated. Recrystallisation of the residue from methylene chloride and 40–60 petrol gave 3-[4-(acetoxycarbonyl)phenyl]-6-[(N-acetyl)isobutylamino]tetrahydro-1,3,5-triazine-2,4-dione in 28% yield, m.p. 134°–137° C.

EXAMPLES 90–91

Using a similar procedure to that described in Example 41 but replacing the acetic anhydride by propionic anhydride or butyric anhydride there may be obtained respectively, 3-(4-methylphenyl)-6-[(N-propionyl)isobutylamino]tetrahydro-1,3,5-triazine-2,4-dione (Example 90) as a solid, m.p. 122°–123° C., in 48% yield, and 3-(4-methylphenyl)-6-[(N-butyryl)isobutylamino]tetrahydro-1,3,5-triazine-2,4-dione (Example 91) as a solid, m.p. 152°–153° C., in 35% yield.

EXAMPLE 92

Ketene gas [generated by pyrolysis of acetone at 600°–700° C. using an apparatus based on that described by Williams and Hurd, *J. Org. Chem.*, 1946, 5, 122–125] was bubbled into a stirred suspension of 3-(4-methylphenyl)-6-isobutylaminotetrahydro-1,3,5-triazine-2,4-dione (2.0 ml.) in methylene chloride (100 ml.) during 50 minutes, to give 1-acetyl-3-(4-methylphenyl)-6-(isobutylamino)tetrahydro-1,3,5-triazine-2,4-dione in situ. The mixture was then stirred at room temperature for 1 hour. Excess ketene was then removed by passing argon gas through the reaction mixture for 1 hour, and the mixture evaporated. The residue obtained was recrystallised from 1,2-dimethoxyethane to give 3-(4-methylphenyl)-6-[(N-acetyl)isobutylamino]tetrahydro-1,3,5-triazine-2,4-dione as a solid (0.87 g.), m.p. 159°–160° C.

EXAMPLES 93–96

1 M-Sodium hydroxide solution (2.4 ml., 2.4 mM) was added to a stirred solution of 3-(4-methylphenyl)-6-[(N-acetyl)isobutylamino]tetrahydro-1,3,5-triazine-2,4-dione (0.79 g., 2.5 mM) in acetone (15 ml.). The mixture was then stirred at room temperature for 15 minutes and was then evaporated. The residue was triturated with tetrahydrofuran (5–10 ml.) to give 3-(4-methylphenyl)-6-[(N-acetyl)isobutylamino]tetrahydro-1,3,5-triazine-2,4-dione sodium salt (Example 93) as a white solid (0.46 g.), m.p. 192°–195° C. (after drying over phosphorus pentoxide).

Using a similar procedure, the sodium salt of 3-(4-methoxyphenyl)-6-[(N-acetyl)isobutylamino]tetrahydro-1,3,5-triazine-2,4-dione (Example 94) was obtained as a white solid, m.p. 185°–188° C., in 55% yield.

Using an analogous procedure but replacing sodium hydroxide solution by 1 M-potassium hydrogen carbonate solution, there were obtained:

(a) the potassium salt of 3-(4-methylphenyl)-6-[(N-acetyl)isobutylamino]tetrahydro-1,3,5-triazine-2,4-dione (Example 95) as a solid, m.p. 257°–259° C., in 22% yield, and (b) the potassium salt of 3-(4-methoxyphenyl)-6-[(N-acetyl)isobutylamino]tetrahydro-1,3,5-triazine-2,4-dione (Example 96) as a solid, m.p. 268°–269° C., in 86% yield.

EXAMPLE 97

A mixture of 50 parts by weight of 3-(4-methylphenyl)-6-[(N-acetyl)isobutylamino]tetrahydro-1,3,5-triazine-2,4-dione, 27 parts by weight of lactose, and 20 parts by weight of maize starch was thoroughly stirred, and a paste formed from 2 parts by weight of maize starch and 40 parts by weight of water was added and thoroughly mixed. The resulting mass was passed through a 16-mesh screen, dried at 60° C. to constant weight and then passed through a 20 mesh screen. 1 Part by weight of magnesium stearate was added to the granules thus obtained and the mixture was compressed by conventional means, into tablets containing 10, 50, 100 and 200 mg. of active ingredient, suitable for oral administration for therapuetic purposes.

EXAMPLE 98

A mixture of 50 parts by weight of 3-(4-methoxyphenyl)-6-[(N-acetyl)isobutylamino]tetrahydro-1,3,5-triazine-2,4-dione, 33 parts by weight of calcium phosphate, 10 parts by weight of microcrystalline cellulose and 4 parts by weight of calcium carboxymethylcellulose was thoroughly stirred and a paste formed from 2 parts by weight of polyvinylpyrrolidone and 40 parts by weight of water was added and thoroughly mixed. The resulting mass was passed through a 16-mesh screen, dried at 60° C. to constant weight and then passed through a 20-mesh screen. 1 Part by weight of magnesium stearate was added to the granules thus obtained and the mixture was compressed by conventional means, into tabelets containing 10, 50, 100 and 200 mg. of active ingredient, suitable for oral administration for therapeutic purposes.

EXAMPLE 99

The procedure of Example 97 or 98 may be repeated using as active ingredient another compound of formula I or a pharmaceutically acceptable salt thereof, for example as specified in any one of the preceding Examples.

What is claimed is:

1. A 6-acylamino-tetrahydro-1,3,5-triazine-2,4-dione of the formula:

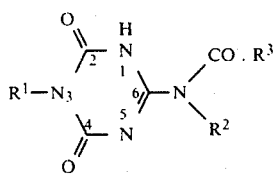

wherein $R^1$ is a phenyl or phenyl-(1-4C)alkyl radical optionally bearing one or two substituents selected from halogeno, trifluoromethyl, (1-4C)alkyl, (1-4C)alkoxy, methylenedioxy, (2-5C)alkanoyloxy, nitro, acetyl, cyano, phenyl, halogenophenyl, carboxy, [(1-4C)alkoxy]-carbonyl, (3-6C)alkenloxy, (2-8C)dialkylamino, and (1-4C)alkylthio substituents, a phenyl radical bearing three, four or five fluoro substituents, or a naphthyl, furyl, thienyl, pyridyl, quinolinyl, benzthienyl or (furyl-, thienyl-, pyridyl-, quinolinyl- or benzthienyl)-(1-4-C)alkyl radical optionally bearing a substituent selected from halogeno, (1-4C)alkyl and (1-4C)alkoxy substituents; and wherein $R^2$ is a (3-8C)alkyl radical or a (1-4-C)alkyl radical bearing one or two (1-4C)alkoxy substituents or bearing a 1,3-dioxalanyl, tetrahydrofuryl or tetrahydropyranyl substituent, or is a (3-8C)cycloalkyl, [(3-8C)cycloalkyl]-(1-4C)alkyl, (3-6C)alkenyl radical, or is a phenyl-(1-4C)alkyl or phenyl radical optionally bearing a substituent selected from halogeno, trifluoromethyl, (1-4C)alkyl and (1-4C)alkoxy substituents; and $R^3$ is a (1-4C)alkyl radical; or a pharmaceutically acceptable base-addition salt thereof; or when $R^1$ is a radical bearing a (2-8C)dialkylamino substituent, a pharmaceutically acceptable acid-addition salt thereof.

2. A compound of formula I as claimed in claim 1 wherein $R^1$ is a phenyl, benzyl, 1-(phenyl)ethyl or 2-(phenyl)ethyl radical optionally bearing one or two substituents selected from fluoro, chloro, bromo, trifluoromethyl, methyl, ethyl, methoxy, ethoxy, methylenedioxy, acetoxy, propionyloxy, butyryloxy, nitro, acetyl, cyano, phenyl, chlorophenyl, carboxy, methoxycarbonyl, ethoxycarbonyl, allyloxy, dimethylamino, diethylamino, and methylthio substituents, a 2,4,6-trifluoro-, 2,4,5,6-tetrafluoro- or 2,3,4,5,6-pentafluoro-phenyl radical, or a naphthyl, fur-2-yl, fur-3-yl, thien-2-yl, thien-3-yl, pyrid-3-yl, quinolin-6-yl, benzthien-2-yl or benzthien-3-yl or (fur-2-yl, fur-3-yl, thien-2-yl, thien-3-yl, pyrid-3-yl, quinolin-6-yl, benzthien-2-yl or benzthien-3-yl)-methyl, -1-ethyl or -2-ethyl radical optionally bearing a substituent selected from fluoro, chloro, bromo, methyl, ethyl, methoxy and ethoxy radicals; and wherein $R^2$ is an n-propyl, isobutyl, n-butyl, sec-butyl, n-pentyl, pent-2-yl, pent-3-yl or neopentyl radical, or a methyl or ethyl radical bearing one or two methoxy or ethoxy substituents, or bearing a 1,3-dioxalan-2-yl, tetrahydrofur-2-yl, tetrahydropyran-2-yl or tetrahydropyran-3-yl radical, or $R^2$ is a cyclopropyl, cyclohexyl, cyclohexylmethyl, allyl, 2-methylallyl, or is a benzyl, 1-phenylethyl, 2-phenylethyl or phenyl radical optionally bearing a substituent selected from fluoro, chloro, bromo, trifluoromethyl, methyl, ethyl, methoxy and ethoxy substituents; and $R^3$ is a methyl, ethyl or propyl radical.

3. A compound of formula I as claimed in claim 1 wherein $R^1$ is a phenyl, 2-chlorophenyl, 4-chlorophenyl, 4-fluorophenyl, 2,4-difluorophenyl, 2,3,4,5,6-pentafluorophenyl, 3-trifluoromethylphenyl, 2-methylphenyl, 3-methylphenyl, 4-methylphenyl, 4-ethylphenyl, 2,6-dimethylphenyl, 2-methoxyphenyl, 3-methoxyphenyl, 4-methoxyphenyl, 4-ethoxyphenyl, 3,4-methylenedioxyphenyl, 4-acetoxyphenyl, 4-nitrophenyl, 4-cyanophenyl, 4-(4-chlorophenyl)phenyl, 4-carboxyphenyl, 4-(ethoxycarbonyl)phenyl, 4-allyloxyphenyl, 4-dimethylaminophenyl, 4-methylthiophenyl, benzyl, 1-(phenyl)ethyl, 4-methoxybenzyl, naphth-2-yl, fur-2-yl, thien-2-yl, thien-3-yl, 2-chloropyrid-3-yl, quinol-6-yl, (thien-2-yl)methyl, (fur-2-yl)methyl or benzthien-2-yl radical.

4. A compound of formula I as claimed in claim 1 wherein $R^1$ is a phenyl or phenyl(1-4C)alkyl radical optionally bearing one or two substituents selected from halogeno, trifluoromethyl, (1-4C)alkyl, (1-4C)-alkoxy, methylenedioxy, acetoxy, nitro, acetyl, cyano, phenyl, halogenophenyl and carboxy substituents, or a naphthyl, furyl, thienyl, pyridyl, quinolinyl, benzthienyl or (furyl-, thienyl-, pyridyl-, quinolinyl- or benzthienyl)-(1-4C)alkyl radical optionally bearing a substituent selected from halogeno, (1-4C)alkyl and (1-4C)alkoxy substituents; $R^2$ is a (3-8C)alkyl radical; and $R^3$ is a methyl radical; or a pharmaceutically acceptable base-addition salt thereof.

5. A compound of formula I as claimed in claim 1 wherein $R^1$ is a phenyl radical optionally bearing a substituent selected from halogeno, (1-4C)alkyl, (1-4C)alkoxy and trifluoromethyl substituents, or is a thien-2-yl radical.

6. A compound as claimed in claim 1 wherein $R^2$ is an isopropyl, isobutyl, sec-butyl or pent-3-yl radical, and $R^3$ is a methyl radical.

7. A compound selected from the group consisting of 3-(thien-2-yl)-6-[(N-acetyl)pent-3-ylamino]tetrahydro-1,3,5-triazine-2,4-dione and the pharmaceutically acceptable base-addition salts thereof.

8. A base-addition salt of a compound of formula I as claimed in claim 1 which is an alkali metal, alkaline earth metal or aluminium salt, a copper salt or a complex therewith, or a salt of an organic base affording a pharmaceutically acceptable cation.

9. A method for producing an analgesic effect in a warm-blooded animal requiring such treatment which comprises administering to said animal an effective amount of a compound of formula I or a pharmaceutically acceptable salt thereof, as defined in claim 1.

10. A pharmaceutical composition which comprises a compound of formula I or a pharmaceutically acceptable salt thereof as defined in claim 1, together with a pharmaceutically acceptable diluent or carrier.

11. A compound selected from the group consisting of 3-(thien-2-yl)-6-[(N-acetyl)-isobutylamino]tetrahydro-1,3,5-triazine-2,4-dione, and the pharmaceutically acceptable base-addition salts thereof.

12. A compound selected from the group consisting of 3-(4-methylphenyl)-6-[(N-acetyl)isobutylamino]tetrahydro-1,3,5-triazine-2,4-dione, and the pharmaceutically acceptable base-addition salts thereof.

13. A compound selected from the group consisting of 3-(4-methoxyphenyl)-6-[(N-acetyl)isobutylamino]tetrahydro-1,3,5-triazine-2,4-dione, and the pharmaceutically acceptable base-addition salts thereof.

14. A compound selected from the group consisting of 3-(3-methoxyphenyl)-6-[(N-acetyl)isobutylamino]tetrahydro-1,3,5-triazine-2,4-dione, and the pharmaceutically acceptable base-addition salts thereof.

* * * * *

UNITED STATES PATENT AND TRADEMARK OFFICE
CERTIFICATE OF CORRECTION

PATENT NO. : 4,254,122

DATED : March 3, 1981

INVENTOR(S) : Edward D. Brown

It is certified that error appears in the above-identified patent and that said Letters Patent is hereby corrected as shown below:

In regard to Formulae II and III, change "$R^1$" to --Q-- at the following places:

Column 9, lines 32 and 55, in table headings
Column 10, line 54, in table heading
Column 11, lines 28 and 38
Column 12, lines 19 and 41, in table headings
Column 13, lines 5 and 16, in table headings
Columns 15-16, lines 58 and 63, in table heading
Column 17, line 3, table heading; and lines 44, 49, 51
Column 18, line 44 in table heading Signed and Sealed this Twentieth Day of August 1985

[SEAL]

Attest:

DONALD J. QUIGG

Attesting Officer — Acting Commissioner of Patents and Trademarks